United States Patent [19]

Katayama et al.

[11] Patent Number: 4,613,588
[45] Date of Patent: Sep. 23, 1986

[54] BENZALDEHYDE AND 4,6-O-BENZYLIDENE-D-GLUCOSE FOR ALLEVIATING PAIN

[75] Inventors: Takashi Katayama, Tokyo; Tadahiko Hazato, Wako, both of Japan

[73] Assignee: Kaken Pharmaceutical Co. Ltd., Japan

[21] Appl. No.: 750,327

[22] Filed: Jun. 28, 1985

[30] Foreign Application Priority Data

Jun. 28, 1984 [JP] Japan ................ 59-131891

[51] Int. Cl.[4] ............ A61K 31/11; A61K 31/70

[52] U.S. Cl. .................. 514/23; 514/698; 514/699

[58] Field of Search .............. 514/23, 698, 699

Primary Examiner—Stanley J. Friedman
Attorney, Agent, or Firm—Jacobs & Jacobs

[57] ABSTRACT

Benzaldehyde and 4,6-O-benzylidene-D-glucose have been found to have analgesic activity. It is believed that this analgesic activity results from the inhibition of enkephalinase. Therefore benzaldehyde and 4,6-O-benzylidene-D-glucose are also useful for inhibiting enkephalinase in humans.

8 Claims, No Drawings

BENZALDEHYDE AND 4,6-O-BENZYLIDENE-D-GLUCOSE FOR ALLEVIATING PAIN

Benzaldehyde and 4,6-O-benzylidene-D-glucose are known compounds. According to Japanese Patent Application Laid-Open No. 108027/1977 and No. 70428/1979, respectively, these two substances are known to have carcinostatic effect.

It is also known in the art that there is a receptor which will combine with morphine in the human brain. The presumption is that a morphine-like substance is also present in humans and animals. In 1975 a peptide having an opioid effect was discovered in pig and cow brains by J. Hughes et al. They succeeded in identifying the peptide and named the substance enkephalin.

Enkephalin has a structure composed of five amino acids of Tyr-Gly-Gly-Phe-Leu (or -Met), and for the past several years the presence of many enkephalin homologs has been found. Takagi et al have discovered that Kyotorphin (Try-Arg) is present in the brain and exhibits an analgesic effect. However, is known to be rapidly decomposed by enzymes and loses it physiological activity. It has been found that in the Macaca Fascicularis brain, the human cerebrospinal fluid, the human small intestinal longitudinal muscle and the human and guinea pig blood, there are present aminopeptidase Tyr from the N-terminal of enkephalin, dipeptidylaminopeptidase Tyr-Gly, carboxypeptidase Leu or Met from the C-terminal and dipeptidylcarboxypeptidase Phe-Leu (or -Met), and these properties have been studied. The present invention is based on a surprising discovery that benzaldehyde and its D-glucose acetal, namely, 4,6-O-benzylidene-D-glucose produces analgesic effects when administered to humans and animals. The substance has been found to be particularly useful in effecting analgesia in humans, especially those whose pain is from carcinomatous origin.

It is believed that the analgesic effects result from an inhibiting effect from enkephalinase A out of dipeptidylcarbonylpeptitase. It therefore appears that benzaldehyde and 4,6-O-benzylidene-D-glucose inhibit enkephalinase present in the brain and therefore by administering an analgesically effective amount of benzaldehyde or 4,6-O-benzylidene-D-glucose pain will be alleviated and an analgesic effect results.

More particularly, the present invention resides in analgesic pharmaceutical compositions comprising an analgesic pharmaceutical composition for administration to humans and animals which comprises an analgesically effective amount of benzaldehyde or 4,6-O-benzylidene-D-glucose in combination with a pharmaceutically acceptable or veterinarily acceptable carrier. The analgesic pharmaceutical compositions of the present invention are particularly useful for alleviating pain in humans.

According to one embodiment of the present invention, the compositions according to the present invention contain benzaldehyde in combination with a stabilizing amount of cyclodextrin. According to a further embodiment of the present invention an analgesically effective amount of 4,6-O-benzylidene-D-glucose is combined with a pharmaceutically acceptable carrier.

The present invention also includes a method which comprises administering benzaldehyde in combination with a stabilizing amount of cyclodextrin. According to a further embodiment of the present invention, pain is alleviated in humans by administering benzaldehyde in combination with a stabilizing amount of cyclodextrin and a pharmaceutically acceptable carrier. According to a further embodiment of the present invention, pain is alleviated in humans by administering an analgesically effective amount of 4,6-O-benzylidene-D-glucose in combination with a pharmaceutically acceptable carrier.

According to a further embodiment of the present invention, enkephalinase is inhibited by administering a therapeutically effective amount of benzaldehyde or 4,6-O-benzylidene-D-glucose in combination with a pharmaceutically acceptable carrier. According to a further embodiment of this method, benzaldehyde in combination with a stabilizing amount of cyclodextrin is administered to humans. According to a further embodiment of this method, 4,6-O-benzylidene-D-glucose is administered to humans.

According to the present invention, benzaldehyde and 4,6-O-benzylidene-D-glucose may be formulated into pharmaceutical compositions for the administration to humans or animals by combining the active agent with a pharmaceutically acceptable or veterinarily acceptable carrier. The compositions may be in the form of tablets, capsules, granules, powder or other forms suitable for oral administration. They are prepared by conventional procedures. Intravenous, infusion and rectally administrable compositions are also prepared by conventional procedures well known in the pharmaceutical art. When benzaldehyde is used as the active agent it is preferred that it be combined with a stabilizing amount of cyclodextrin since benzaldehyde is itself unstable and has an unpleasant odor. The cyclodextrin stabilizes the benzaldehyde and also helps to mask the unpleasant odor. Benzaldehyde is preferably administered orally and the D-glucose acetal intravenously.

Since both benzaldehyde and 4,6-O-benzylidene-D-glucose are substantially non-toxic a wide dosage range may be administered depending on the severity of the pain experienced. The acute toxicity of benzaldehyde and 4,6-O-benzylidene-D-glucose are 5 g/kg or higher and 4 g/kg or higher, respectively, when measured by subcutaneous injection in rats according to conventional toxicity procedures. In addition, benzaldehyde and 4,6-O-benzylidene-D-glucose appear to be rapidly metabolized and hence excreted from the body thereby further reducing any tendency to contraindications.

Benzaldehyde and 4,6-O-benzylidene-D-glucose may be administered as the sole analgesic agent or may be administered in combination with one or more additional analgesic agents. The compositions and methods of the present inventions are particularly useful for treating pain due to various cancers, peptic and duodenal ulcers, renal and urethral calculus, arteritis obliterans and the like, pain following operations, pain resulting from the use of diagnostic instruments in the stomach, urinary tract, bladder and the like and pain resulting from the administration of various drugs.

Since benzaldehyde and 4,6-O-benzylidene-D-glucose have excellent antitumor activity they are paticularly useful for alleviating carcinomatous pain. The amount of benzaldehyde and 4,6-O-benzylidene-D-glucose to be administered would depend on a variety of factors including the past medical history of the patient, the severity of the pain and the cause thereof. Generally, from about 100 to 2500 mg one to four times per day would be the dosage range for an average human adult. A particularly useful dosage range has been found to be about 500 mg per day for a human adult preferably administered in four doses of approximately 125 mg per dose.

The following non-limitative example more particularly illustrates the present invention:

TEST EXAMPLE

Enkephalinase Inhibiting Effect (1) Preparation of Enzymes

The cerebrum of Macaca Fascicularis was chopped using anatomical scissors, 3 volumes that of 25 mM tris-hydrochloric acid buffer (pH 7.7) was added thereto and the mixture homogenized. It was then ultra-centrifuged (50,000×g), the supernatant was removed, and the obtained precipitants were treated and washed twice using the same buffer (these precipitates contained enkephalin decomposing enzymes in a form combined to the cell membrane).

Thereafter, 25 mM tris-hydrochloric acid buffer (pH 7.7) containing 1% of Triton X-100 was added to the precipitates to extract enkephalinase. The extract containing the crude enzyme was subjected to separating and purifying operations using a DE-52 cellulose column (produced by Pharmacia Fine Chemicals) and various columns, to obtain four kinds of enkephalin decomposing emzymes, namely aminopeptidase hydrolyzing the first one from the N-terminal of enkephalin to liberate Tyr, dipeptidylaminopeptidase (enkephalinase B) hydrolyzing the second to liberate Tyr-Gly and dipeptidylcarboxylpeptidase hydrolyzing the second from the C-terminal to liberate Try-Gly-Gly (angiotensin converting enzyme and enkephalinase A).

The obtained enkephalin decomposing enzymes were analyzed by acrylamide electrophoresis to find that they were single proteins respectively.

(2) Measurement of Enzyme Activity

The enzymatic activity of the respective decomposing enzymes obtained above was measured by the qualitative and quantitative analyses of the decomposition products using [$^3$H]-enkephalin or enkephalin as a substrate and employing Porapak Q (produced by Water Associates) column method, high-performance liquid chromatography (HPLC), silica gel thin layer autography, etc.

For example, the enzymatic activity of enkephalinase A was measured as follows:

10 μl of 10 μCi [$^3$H] Leu-enkephalin, 20 μl of 2.5 mM tris-hydrochloric acid buffer and 30 μl of water were mixed at 37° C. for 5 minutes, 30 μl of the enkephalinase A enzyme solution obtained in the above (1) was added and incubated at 37° C. for an hour. Thereafter, 20 μl of 30% acetic acid was added thereto, and the mixture was subjected to a Porapak Q column, and the hydrolyzed [$^3$H] Tyr-Gly-Gly was determined using a liquid scintillation counter.

(3) Enzyme Inhibiting Effects of the Compounds of the Invention

Aqueous solutions of benzaldehyde and 4,6-O-benzylidene-D-glucose were added respectively to the enzymatic activity measuring systems of the above (2) using the enzyme solutions of 4 kinds of the enkephalin decomposing enzymes, and the effects to inhibit to the enzymatic activity were studied respectively.

As a result, benzaldehyde at a concentration of 1 mg/ml did not exhibit an enzyme inhibiting effect on aminopeptidase, dipeptidylaminopeptidase (enkephalinase B) and angiotensin converting enzyme, but exhibited an almost complete (99%) inhibiting effect on dipeptidylcarboxypeptidase (enkephalinase A). Further, 4,6-O-benzylidene-D-glucose at a concentration of 1.2 mg/ml did not exhibit an enzyme inhibiting effect on aminopeptidase, dipeptidylaminopeptidase (enkephalinase B) and angiotensin converting enzyme like benzaldehyde but exhibited an enzyme inhibiting effect of 81% on dipeptidylcarboxypeptidase (enkephalinase A).

This data demonstrates that benzaldehyde and 4,6-O-benzylidene-D-glucose have an enzyme inhibiting effect on enkephalinase A.

FORMULATION EXAMPLE 1

Injections and Infusions

Benzaldehyde and powdered glucose are aseptically allotted into vials so that each vial contains 500 mg of benzaldehyde and 5 g of powered glucose, sealed, and, after sealing in an inert gas such as nitrogen, helium, etc., stored in a dark, cold place. Before use, 100 ml of 0.85% physiological saline is added to prepare an intravenous injection, and it is administered at a dose of 2–100 ml per day depending on the condition by intravenous injection or infusion.

FORMULATION EXAMPLE 2

Injections and Infusions

Intravenous injections are prepared in a manner similar to that in Formulation Example 1 except that the benzaldehyde is replaced by 1 g of 4,6-O-benzylidene-D-glucose and they are administered at a dose of 2–100 ml per day depending on the condition by intravenous injection or infusion.

FORMULATION EXAMPLE 3

Capsules

A mixture of 30 mg of benzaldehyde dissolved in 1 g of refined sesame oil and 100 mg of aluminum stearate gel is allotted into capsules, in amounts of 0.5 ml respectively, to prepare enteric capsules. The capsules are orally administered.

FORMULATION EXAMPLE 4

Capsules

Following the procedure of Formulaton Example 3, 200 mg of 4,6-O-benzylidene-D-glucose was used to prepare capsules.

FORMULATION EXAMPLE 5

Enteric Tablet 25 g of benzaldehyde is added to 3,000 ml of a saturated aqueous solution of β-cyclodextrin (produced by Nippon Maize Products Co., Ltd.) and stirred and mixed for 5 hours thereby an inclusion product is precipitated. This precipitated product is dried under reduced pressure to obtain about 300 g of an inclusion compound of benzaldehyde.

Using the following components compositions, enteric tablets for adults (a) and for children (b) are prepared, in quantities of 1,000 tablets respectively,

|  | (a) | (b) |
|---|---|---|
| [A] | | |
| Main Agent (Inclusion Compound of Benzaldehyde) | 300.0 (g) | 150.0 (g) |
| Lactose | 298.2 | 149.1 |

-continued

|  | (a) | (b) |
|---|---|---|
| Hydroxypropyl Cellulose | 1.8 | 0.9 |
| Magnesium Stearate | 6.0 | 3.0 |
| [B] | | |
| Cellulose Acetate Phthalate | 18.0 (g) | 12.0 (g) |
| Hydroxypropylmethyl Cellulose Phthalate | 18.0 | 18.0 |

The respective components of [A] are taken and thoroughly mixed, the obtained mixture is then either directly compressed, or well kneaded, granulated through an extruding granulater screen, well, well dried and compressed, to prepare tablets.

Thereafter the formed tablets are coated with the base composed of the uniformly dissolved components [B] to prepare enteric tablets.

FORMULATION EXAMPLE 6

Enteric Tablets

Enteric tablets are prepared in a manner similar to that in Formulation Example 5 except that 15 g of 4,6-O-benzylidene-D-glucose is used.

Further, using benzaldehyde and 4,6-O-benzylidene-D-glucose the following carcinomatous pain treating tests were conducted.

CLINICAL EXAMPLE 1

Patient: Male, born in 1910.
Diagnosis: Relapse of mandible.

The patient underwent two operations on mandible cancer, but experienced a relapse. He was again admitted to the hospital because severe pain continued and he could not eat normally. Intubation feeding was conducted while alleviating the pain by morphine injection.

After hospitalization, 25 mg benzaldehyde tablets (enteric tablets containing benzaldehyde prepared in the above-described Formulation Example 5) were administered at a dosage of 5 tablets, 4 times a day.

From the 5th day after the start of administration, the patient claimed an improvement of the subjective symptom as he felt the pain was eased, the administration of the morphine was ceased and only benzaldehyde was continuously dosed.

On the 7th day he felt almost no pain and was now able to eat soft food and thus the intubation was ceased.

He tried to refuse the third operation since the subjective symptom of the pain was reduced by dosing of benzaldehyde. However, since the X-ray examination revealed that the carcinoma did not reduce in size, the operation was practiced according to the advice of the surgeon.

CLINICAL EXAMPLE 2

Patient: Male, born in 1937.
Diagnosis: Metastasis of gastric cancer to the bone.

The patient suffered from gastric cancer and the stomach was completely extirpated, but since the cancer was spread to the pelvis, the right calf, etc. and hip pain and tenderness on pressure became severe, he became confined to bed.

Since variety of chemotherapeutics were not administered because there was a threat of strong side effects, the sole administration of 4,6-O-benzylidene-D-glucose was started in such a way that 1,200 mg of a freeze dried preparation thereof was dissolved in 100 ml of physiological saline and administered i.v. at a rate of once a day (time required being ca. 10 minutes).

From the 10th day after the start of dosing, he became able to sit on bed, then on the 17th to 18th day the pain almost disappeared and he became able to walk, and on the 26th day he was released from the hospital.

The diagnosis of the bone by scintillation on that occasion revealed that the tumor condition was the same as compared with before the administration of 4,6-O-benzylidene-D-glucose.

What is claimed is:

1. A method of effect analgesia in humans and animals which comprises administering to a human or animal in need thereof an analgesically effective amount of benzaldehyde or 4,6-O-benzylidene-D-glucose in combination with a pharmaceutically acceptable or veterinarily acceptable carrier.

2. A method according to claim 1 which comprises administering benzaldehyde in combination with a stabilizing amount of cyclodextrin.

3. A method according to claim 1 of effecting analgesia in humans which comprises administering to a human in need thereof an analgesically effective amount of benzaldehyde or 4,6-O-benzylidene-D-glucose in combination with a pharmaceutically acceptable carrier.

4. A method according to claim 1 of effecting analgesia in humans which comprises administering to a human in need thereof an analgesically effective amount of benzaldehyde in combination with a stabilizing amount of cyclodextrin and a pharmaceutically acceptable carrier.

5. A method according to claim 1 of effecting analgesia in humans which comprises administering to a human in need thereof an analgesically effective amount of 4,6-O-benzylidene-D-glucose in combination with a pharmaceutically acceptable carrier.

6. A method of inhibiting enkephalinase in humans which comprises administering to a human in need thereof a therapeutically effective amount of benzaldehyde or 4,6-O-benzylidene-D-glucose in combination with a pharmaceutically acceptable carrier.

7. A method according to claim 6 which comprises administering benzaldehyde in combination with a stabilizing amount of cyclodextrin.

8. A method according to claim 6 which comprises administering 4,6-O-benzylidene-D-glucose.

* * * * *